United States Patent [19]

Preda

[11] Patent Number: 5,780,255
[45] Date of Patent: Jul. 14, 1998

[54] PROTEIN C PATHWAY SCREENING TEST

[75] Inventor: Luigi Preda, Verano Brianza, Italy

[73] Assignee: Instrumentation Laboratory, S.p.A., Italy

[21] Appl. No.: 488,510

[22] Filed: Jun. 9, 1995

[51] Int. Cl.$^6$ .............................. C12Q 1/37; C12Q 1/56; C12N 9/48; C12N 9/74
[52] U.S. Cl. ........................ 435/23; 435/13; 435/212; 435/214; 530/384
[58] Field of Search .................... 435/23, 13, 291, 435/212, 214; 530/384

[56] References Cited

U.S. PATENT DOCUMENTS

| | | | |
|---|---|---|---|
| 3,983,004 | 9/1976 | Trobisch et al. | 195/99 |
| 4,011,142 | 3/1977 | Jacobi | 195/103.5 |
| 4,033,824 | 7/1977 | Karges et al. | 195/99 |
| 4,056,484 | 11/1977 | Heimburger et al. | 252/408 |
| 4,106,990 | 8/1978 | Karges et al. | 195/63 |
| 4,334,018 | 6/1982 | Kirchhof | 435/13 |
| 4,692,406 | 9/1987 | Becker et al. | 435/13 |
| 4,784,944 | 11/1988 | Kolde | 435/13 |
| 4,849,403 | 7/1989 | Stocker et al. | 514/2 |
| 5,001,069 | 3/1991 | Bartl et al. | 436/86 |
| 5,049,506 | 9/1991 | Stüber | 436/69 |
| 5,147,805 | 9/1992 | Preda et al. | 436/86 |
| 5,200,322 | 4/1993 | Matsumoto | 435/13 |
| 5,204,240 | 4/1993 | Stüber | 435/13 |
| 5,206,140 | 4/1993 | Marder et al. | 435/7.1 |
| 5,292,664 | 3/1994 | Fickenscher | 436/69 |
| 5,506,146 | 4/1996 | Josef | 436/69 |

FOREIGN PATENT DOCUMENTS

| | | |
|---|---|---|
| 2037434 | 9/1991 | Canada. |
| 2155503 | 2/1996 | Canada. |
| 2162531 | 5/1996 | Canada. |
| 0 076 042 | 4/1983 | European Pat. Off.. |
| 0 107 383 | 5/1984 | European Pat. Off.. |
| 0152612 | 2/1990 | European Pat. Off.. |
| 0406971 A1 | 1/1991 | European Pat. Off.. |
| 0434377 A1 | 6/1991 | European Pat. Off.. |
| 0123883 | 9/1991 | European Pat. Off.. |
| 2 689 640 | 8/1993 | France. |
| WO91/01382 | 2/1991 | WIPO. |
| WO93/07491 | 4/1993 | WIPO. |

OTHER PUBLICATIONS

P.S. Gable et al., "A Protac–Based Screening Test for Activated Protein C Resistant Factor Va", *J. Invest. Medicine: the Official Publn. of the Am. Fed. for Clin. Res. 43* Supp.2:233a (1995)—abstract only.
International Search Report dated Nov. 26, 1996 in corresponding PCT application PCT/US96/09036.

P. P. Deutz–Terlouw et al., "Two ELISA's for Measurement of Protein S, and Their Use in the Laboratory Diagnosis of Protein S Deficiency" *Clinica Chimica Acta* 186:321–334 (1989).

F. Espana et al., "Determination of Plasma Protein C Inhibitor and of Two Activated Protein C–Inhibitor Complexes in Normals and in Patients with Intravascular Coagulation and Thrombotic Disease" *Thrombosis Research* 59:593–608 (1990).

W. Kisiel et al., "Characterization of a Protein C Activator from *Agkistrodon Contortrix Contortrix* Venom" *The Journal of Biological Chemistry* 262 No.26:12607–12613 (1987).

J.L. Martinoli et al., "Fast Functional Protein C Assay Using Protac®, A Novel Protein C Activator" *Thrombosis Research* 43:253–264 (1986).

S. Rosen et al., "Multicenter Evaluation of A Kit for Activated Protein C Resistance on Various Coagulation Instruments Using Plasmas from Healthy Individuals" *Thrombosis and Haemostasis* 72(2):255–260 (1994).

W. Thiel et al., "A Simplified Functional Assay for Protein C in Plasma Samples" *Blut* 52:169–177 (1986).

*Primary Examiner*—Robert A. Wax
*Assistant Examiner*—Lisa J. Hobbs
*Attorney, Agent, or Firm*—Testa, Hurwitz & Thibeault, LLP

[57] ABSTRACT

The present invention provides a method for determining thrombotic risk in an individual. The method involves determining the activity of Protein C and Protein S in the plasma of the individual thought to be at thrombotic risk by adding to a plasma sample obtained from the individual (i) a first reagent in an amount sufficient to induce or activate coagulation in the plasma, (ii) a second reagent which activates endogenous protein C in the plasma, and (iii) a third reagent comprising calcium salts, phospholipids or tissue thromboplastin, or a combination thereof. To a second plasma sample from the same subject is added a reagent which induces or activates coagulation, and a buffer or other material which does not activate protein C, and a third reagent as described above. The time, rate or both, necessary for the conversion of endogenous fibrinogen to fibrin in both the first and second samples is measured. The same steps are performed on normal control plasma, and the difference or ratio in the times, rates, or both, obtained above are determined. The difference or ratio is indicative of the thrombotic risk in the subject. A kit adapted to carry out the method also is the subject of the present invention. The methods and kits of the invention in other embodiments may comprise a first reagent comprising a synthetic substrate, a second reagent which in the first sample from the subject activates protein C, and in the second sample, a second reagent which does not activate protein C. In these embodiments, the rates of hydrolysis of the synthetic substrates are measured and compared.

6 Claims, 1 Drawing Sheet

| C.U.C. % | Ta To SEC | To SEC | Ta SEC |
|---|---|---|---|
| 0 | -2.0 | 40.4 | 33.4 |
| 15 | 6.6 | 40.2 | 46.8 |
| 30 | 21.2 | 40.8 | 62.0 |
| 60 | 53.8 | 40.6 | 94.4 |
| 100 | 98.8 | 38.4 | 137.2 |
y - INTERCEPT = 6.68
SLOPE = 0.962
$r^2 = 0.994$
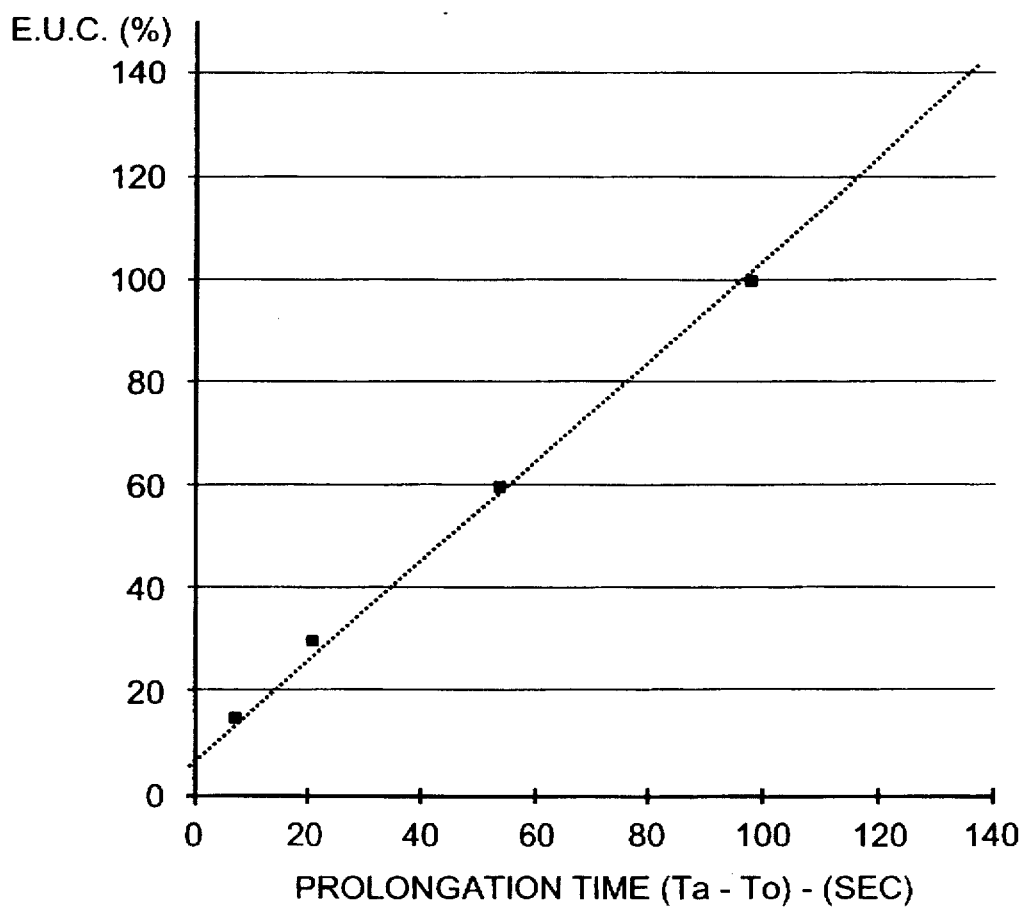
CALIBRATION CURVE

PROTEIN C PATHWAY SCREENING TEST

BACKGROUND OF THE INVENTION

The present invention relates to an analytical global test to determine the risk of thrombosis in an individual by analysis of the Protein C/Protein S functionality in said individual.

Screening tests for coagulation disorders often are used to target patients at risk for bleeding. Such tests include, for example, the activated partial thromboplastin time (APTT) and the prothrombin time (PT) tests. Screening tests for coagulation disorders, or risk of bleeding are designed to detect a significant abnormality in one or more of the clotting factors and to localize this abnormality to various steps in the coagulation pathway.

As commonly understood, coagulation may occur by two pathways, the intrinsic pathway and the extrinsic pathway. The former is generally triggered by the presence of a surface and with the presence of phospholipids and calcium, through a number of steps eventually stimulates the formation of a stabilized fibrin clot. The APTI test typically measures coagulation factors of the intrinsic pathway, where most congenital deficiencies occur, and the PT test measures coagulation factors of the extrinsic pathway.

The APTT test typically is performed by adding an activator such as kaolin, silica, ellagic acid, and the like with phospholipid based reagents, to plasma. This activates Factors XII and XI. Currently, in the APTT, the phospholipids employed are extracted from bovine or rabbit brain, although sources such as soy bean have been used. The exogenous phospholipids of the APTT reagent substitute for the phospholipids provided by platelets in vivo in the activation of Factor X by Factors IX, VIII and V. Blood coagulation is limited in this clotting test by adding calcium. Factor VII is the only factor not affected by partial thromboplastin time. Thus, the APTT is, therefore, normal in patients with a Factor VII deficiency.

The PT test typically is performed by adding tissue thromboplastin with calcium to plasma. This initiates clotting by activating Factor VII, which in turn activatates Factor X which, in the presence of Factor V, leads to the conversion of prothrombin to thrombin. The thrombin which is so produced converts fibrinogen to fibrin. The PT test therefore bypasses the intrinsic clotting pathway and is normal in patients with deficiencies of Factors XII, XI, IX, and VIII. PT is abnormal in patients with deficiencies of Factors VII, X, V, prothrombin or fibrinogen. Tissue thromboplastin is a phospholipid extract (e.g., from rabbit brain or lung or human brain or placenta to which calcium has been added).

Protein C and Protein S (PC and PS, respectively) also are involved in the coagulation process. Protein C is a double-chained, vitamin K-dependent glycoprotein in plasma which is synthesized in the liver. A physiologically indifferent coagulation precursor (decarboxyprotein C) is thereby first formed. Carboxylation of γ-glutamic acid residues in the protein by a vitamin K-dependent carboxylate results in the formation of protein C. Protein C itself is a pro-enzyme and is converted by thrombin into activated protein C. The latter acts as an anti-coagulant by a proteolytic inactivation of the activated coagulation Factors V and VIII. The inhibitory action of the active Protein C is increased by a cofactor, Protein S. Protein S is a single-chained glycoprotein in plasma which is also vitamin K-dependent. Active protein C and protein S form an equimolar complex. A lowered protein C level, as well as protein S level, have been described in patients with liver diseases, disseminated intravascular coagulation (DIC) and after oral anticoagulant therapy. A congenital deficiency of protein C or of protein S results in venous throboembolic risks. Therefore, protein C, as well as protein S play an important part not only in the case of physiological haemostasis, but also in many diseases, and, especially in the case of thrombosis.

In commercially available test processes, the amount of protein C in plasma is determined by enzyme-labelled antibodies. However, this process suffers from the disadvantage that the antibodies used for the determination also react with the above mentioned decarboxyprotein C. Since the plasma concentration of decarboxyprotein C frequently increases very considerably during the course of a treatment with anticoagulants, this process involves a large source of error which, under certain circumstances, can result in false or insufficient therapy.

For example, in some photometric methods, Protein C is activated using Protac® (available from Pentapharm, Switzerland), which is obtained from the venom of the snake *Agkistrodon contortix contortix*, together with a chromogenic protein C substrate. In this process, the preparation of the sample can be omitted, however, it is not possible to differentiate between carboxylated and non-carboxylated protein C. It is known that only carboxylated protein C is effective in vivo. Therefore, no information about the biological activity of the protein C molecule can be obtained with this process.

The amount of protein S in a plasma can be determined by an immunoradiometric test, such as that described, for example, by Bertina et al. (Thromb Haemostas., 52 (2), 268–272/1985). This process, however, suffers from the disadvantage that the antibodies used for the determination also react with nonfunctional protein S, for example with decarboxyprotein S or with protein S complexed with $C_4$-binding protein. Under certain circumstances, this results in falsely positive protein S values. The authors also describe a potential method for determining protein S in plasma in which activated protein C is admixed with human plasma and the partial thromboplastin time (PTT) is determined. The length of the PTT is indicative of the concentration of functional protein S. The reaction can be identified by the cleavage of fibrinogen by thrombin and the formation of a fibrin clot. However, the detection processes are limited, protein C and protein S cannot be simultaneously determined, and purified activated protein C must be used.

Thus, there is a need for a rapid, global test for determing the thrombotic risk in a subject by surveying the activity of all factors, known or unknown on the biochemical mechanisms of coagulation.

SUMMARY OF THE INVENTION

The present invention is directed to an analytical global test for determining the thrombotic risk of a subject by the exploration of protein C/protein S functionality. Additional features and advantages of the invention will be set forth in the description which follows, and in part will be apparent from the description, or may be learned by practice of the invention. The objectives and other advantages of the invention will be realized and attained by the methods and kits particularly pointed out in the written description and claims hereof.

To achieve these and other advantages, and in accordance with the purpose of the invention, as embodied and broadly described herein, the invention provides a method for determining thrombotic risk in a subject by adding to a plasma sample obtained from the subject (i) a first reagent in an amount sufficient to induce or activate coagulation in the plasma, (ii) a second reagent which activates endogenous protein C in the plasma, and (iii) a third reagent comprising calcium salts, phospholipids or tissue thromboplastin, or a combination thereof.

One then adds to a second plasma sample from the same subject (i) a reagent which induces or activates coagulation, (ii) a buffer or other material which does not activate protein C, and (iii) a third reagent comprising calcium salts, phospholipids or tissue thromboplastin, or a combination thereof. The time, rate or both, necessary for the conversion of endogenous fibrinogen to fibrin in both the first and second samples is measured. The same steps are performed on normal control plasma, and the difference or ratio in the times, rates, or both, obtained above are determined In other embodiments, the methods of the invention comprise adding to a plasma sample obtained from the subject a synthetic substrate, and a second reagent which activates protein C in the plasma; and to a second sample from the same subject adding a synthetic substrate and a second reagent which does not activate protein C in the plasma. The rates of hydrolysis of the synthetic substrates in each sample are then measured, and compared as above. The same steps are performed on normal control plasma, and the rates of hydrolysis are determined.

In some embodiments, the first reagent is selected from the group consisting of, but not limited to, Factor IXa, reagents which generate Factor IXa in vitro, and APTT reagents. In other embodiments, the first reagent is selected from the group consisting of Factor Xa, reagents which generate Factor Xa in vitro, PT reagents, and activators of the extrinsic coagulation pathway.

Preferred second reagents may be a purified fraction of venom obtained from a venom producing organism, such as an arachnid or a reptile, i.e. snake or spider venom. In the currently preferred embodiment, the second reagent is a snake venom fraction obtained from *Agkistrodon contortrix contortrix*. In other embodiments, the second reagent may be a recombinant venom protein or polypeptide.

A kit for determining the thrombotic risk in a subject also is the subject of the present invention. In one embodiment, the kit comprises a first container which has (i) a first reagent in an amount sufficient to induce or activate coagulation in a plasma sample obtained from the subject, (ii) a second reagent which activates endogenous protein C in the plasma, and (iii) a third reagent comprising calcium salts, phopholipids or tissue thromboplastin, or a combination thereof.

The kit of the invention further comprises a second container for adding to a second plasma sample from the same subject a first reagent which activates or induces coagulation; a buffer or other material which does not activate protein C; and calcium salts, phospholipids or tissue thromboplastin, or a combination thereof.

In some embodiments, the kit comprises at least one container having therein a first reagent comprising a synthetic substrate, and a second reagent which activates protein C; and at least one second container having therein a first reagent comprising a synthetic substrate, and a second reagent comprising a buffer or other material which does not active protein C. It is understood that the first and second reagents may be combined in a single container (e.g., a vial) or may be provided in separate containers.

The kit may contain first reagents selected from the group consisting of Factor IXa, reagents which generate Factor IXa in vitro and APTT reagents. Alternatively, the first reagent may be selected from the group consisting of Factor Xa, reagents which generate factor Xa in vitro, PT reagents, and activators of the extrinsic coagulation pathway.

In preferred embodiments, the second reagent comprises a purified fraction of venom obtained from a venom producing organism, such as an arachnid or snake. In a curently preferred embodiment, the second reagent is a purified snake venom fraction obtained from *Agkistrodon controtrix contortrix*. The second reagent also may be a recombinant venom protein or polypeptide.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate one embodiment of the invention and together with the description serves to explain the principles of the invention.

BRIEF DESCRIPTION OF THE DRAWINGS

The FIGURE is a calibration curve for the calculation of the coagulative activity, as measured in Equivalent Units of Protein C (EUC), assuming that normal plasma has an activity of 100% EUC, and a plasma deficient in protein C has an activity of 0% EUC.

DETAILED DESCRIPTION OF THE INVENTION

The present invention relates to an analytical global test useful for the exploration of protein C/protein S functionality. The global test can be a diagnostic aid for the evaluation of thrombotic risk in patients suffering from hereditary and non-hereditary thrombophilia (i.e. disorders of the hemopoletic systems in which there is a tendency to the occurrance of thrombosis), or otherwise in patients undergoing particularly pharmacologic treatments such as extroprogestinics, etc. Additionally, patients undergoing surgery can be evaluated to determine thrombotic risk.

The claimed invention is an analytical in vitro test that can be used to diagnose clotting anomalies involved in the inhibitory system, due to either PC deficiency, PS deficiency, or to the presence of molecular anomalies of Factor Va, or to the presence of anti-aPC antibodies. Generally, the methods of the invention provide that patient plasma is incubated with an exogenous reagent able to activate or induce clotting activity; an exogenous reagent that transforms endogenous PC to aPC, and other components such as calcium salts, phospholipids or tissue thromboplastin necessary to complete the clotting reaction. To a second sample of plasma from the same patient is added the first reagent, the third reagent, and in lieu of the second reagent, a substance which does not activate PC, thus showing the patient's global clotting activity. The same steps are repeated using a normal plasma control sample.

The times or rates necessary for the conversion of fibrinogen into fibrin are measured for both samples, and the ratio or difference between the non-activated sample and the activated sample is determined. The ratio or difference is indicative of the presence of potential thrombotic risk. As an example, if the difference in time of the patient plasma sample is shorter than the normal control sample, then there is a high risk of a thrombotic event. The methods and kits of the invention are discussed in further detail below.

The analytical test provides a method for determining the ratio between the clotting activity and the inhibitory activity of the protein C/ protein S system in a plasma sample. In one embodiment, the test involves first adding to a plasma sample from the subject a first reagent sufficient to induce or activate coagulation in the plasma. Any reagent capable of inducing or activating coagulation can be used. Preferred first reagents include, but are not limited to, Factor LXa, reagents which generate Factor IXa in vitro, APTT reagents, Factor Xa, reagents which generate Factor Xa in vitro, PT reagents and activators of the extrinsic coagulation pathway.

Activators of the extrinsic coagulation pathway may be any activators having the desired activity. Specifically, activators useful in the invention may include natural sourced or recombinant tissue thromboplastins, including, for example, bovine thromboplastin, human thromboplastin, rabbit thromboplastin and porcine thromboplastin. Bovine thromboplastin currently is preferred. Portions of such activators may also have the desired activity. A recombinant or synthetic mutant or modified thromboplastin having the desired activity also may be used for this purpose. Mutant or modified thromboplastins are recombinant or synthetic proteins in which a portion of the nucleotide sequence encoding the protein or the amino acid sequence is missing or altered, but which retains thromboplastin activity. One skilled in the art may readily identify other activators of the extrinsic coagulation pathway which would be useful in the claimed invention.

A second reagent also is added to the plasma sample obtained from the subject. The second reagent activates endogenous Protein C in the plasma. The second reagent can be any substance having the desired activity. For example, one may obtain the second reagent from the venom of venom producing organsisms such as arachnids or reptiles. For example, snake venoms from which the desired fraction can be purified may be obtained from *Agistrodon contortrix contortrix, A.C. mokasen, A.C. pictigaster, A. piscivours, A. ieucostoma, A bilineatus, Bothrops moojeni, B. pradoi, Cerastes cerastes, Vipera lebetrina* or *V. russelli*. Preferably, the second reagent is snake venom, most preferably a fraction obtained from *Agkistrodon contortrix contortrix* . Such a reagent is commercially available under the tradename Protac®. The second reagent may, in some instances, be a derivatized or modified form of the venom, or in other embodiments at least a portion of a recombinant venom protein or polypeptide having the desired activity.

The third reagent added to the plasma sample may comprise calcium salts, phospholipids or tissue thromboplastin, or any combination thereof.

A second sample obtained from the same subject is combined with the first reagent which activates coagulation, a buffer or other material which does not activate Protein C, and the third reagent, e.g., calcium salts, phospholipids, or tissue thromboplastin or any combination thereof. One then measures the conversion of endogenous fibrinogen to fibrin in both the first sample and the second sample. The measurements may, for example, determine the rate of conversion, the time of conversion, or both. One skilled in the art can easily select which measurements best suits each individual application. If the third reagent is a synthetic substrate, the hydrolysis of the substrate is measured instead of the conversion of fibrinogen to fibrin.

The rate of time of conversion of fibrinogen to fibrin can be measured by methods known in the art for determining coagulation times or rates, such as, for example, by measurung the change in optical density of the sample.

The difference or ratio between the measurements of the rate or time (or both) obtained above is then calculated, and the identical steps performed on normal control plasma. Then, one determines the difference or ratio 1) in the times, rates (or both) obtained for the normal control, and 2) the first and second samples. The difference is indicative of the thrombotic risk in the subject. If the time, rate, or both, calculated for the test plasma is shorter than the time, rate or both for the normal control plasma, the patient is at increased thrombotic risk.

Specifically, shorter conversion times or rates are indicative of a deficiency in Protein C, Protein S, or both. Lowered or reduced levels of Protein C or Protein S may result in increasing the risk of clot formation. Alternatively, a high level of PC or PS will indicate a normal coagulation pattern, and thus a low risk of thrombosis.

In other embodiments, the methods of the invention comprise adding to a first sample from the subject a synthetic substrate, and a second reagent which activates protein C. The second sample from the subject is combined with a synthetic substrate and a second reagent which does not activate protein C. In these embodiments, the rate of hydrolysis of the synthetic substrate in the first and second samples are measured and compared.

The synthetic substrate, may, for example be a thrombin substrate, useful for monitoring the reaction. Thrombin substrates may include synthetic fibrinogen or portion thereof, or other protein or polypeptide which can be converted by thrombin to a detectable substance. The synthetic substrate may comprise a label or tag such that the rate of hydrolysis of the substrate may be measured. It is contemplated that the label or tag be intrinsic to the substrate, or a detectable moiety attached to the substrate.

The methods of the invention may be carried out manually, or automatically. The methods preferably are carried out automatically using a specially designed instrument, such as those available from Instrumentation Laboratory, S.p.A., Milan, Italy. The samples are loaded into the instrument, and reagents are added, and the conversion times or rates are determined in accordance with the manufacturer's instructions.

The claimed invention also encompasses kits for determining thrombotic risk in a subject. The kits contain a first container having (i)a first reagent in an amount sufficient to induce or activate coagulation in a plasma sample obtained from the subject, (ii) a second reagent which activates endogenous Protein C in the plasma, and (iii) a third reagent comprising calcium salts, phospholipids or tissue thromboplastin, or a combination thereof. The term "container" as used herein means any container capable of housing the reagents listed above. In various embodiments, the first container may comprise a separate vial for each reagent, a single vial with all three reagents, or, two vials containing any combination of the three reagents. One skilled in the art may choose any configuration for the first container, based upon the particular application and convenience of use. The container may optionally be a disposable, single use container, or, in other embodiments, may be a container capable of sterilization and reuse.

The kit of the invention also has a second container for adding to a second plasma sample from the same subject (i) a first reagent, (ii) a buffer or other material which does not activate Protein C, and (iii) a third reagent comprising calcium salts, phospholipids or tissue thromboplastin, or a combination thereof.

The reagents used in the kits may be the same reagents as discussed above in relation to the methods of the invention.

In some embodiments, the kits of the invention have a first container comprising a synthetic substrate and a second reagent which activates protein C. The second container comprises a synthetic substrate and a buffer or material which does not activate protein C. In other embodiments the kits of the invention may contain only one container, i.e. either the first or the second container.

Thus, as described above, the claimed invention allows the rapid evaluation of the functionality of PC and PS in subjects. The tests of the invention can be a valid diagnostic aid for screening patient samples to recognize those patients with high thrombotic risk, i.e. hereditary PC deficiency, hetero-or homozygote, and patients undergoing surgery. The methods of the invention encompass a global test, because they are capable of detecting the influence of other factors, known or unknown, in addition to PC and PS, on the biochemical mechanism that allows effective activated PC inhibiting action on the phsysiological substrates (i.e. factor Va and VIIIa).

The global activity of the system may be measured in equivalent units of protein C, arbitrarily assigning an activity value of 100% to a pool of normal patient plasma and 0% to a PC deficient plasma. Other means of measurement may be used to obtain the relative activity of the PC/PS system, and are easily determined by the skilled artisan.

EXAMPLE

The analytical test below can be carried out either manually or automatically. The volumes reported below were obtained using the Research Program of the ACL 3000/p system (available from Instrumentation Laboratory, S.p.A., Milan, Italy).

50 µL of undiluted patient plasma were separately loaded in a rotor with 50 µL of $H_2O$ (or similar buffer), and centrifuged. After 150 seconds, 50 µL of calcium bovine thromboplastin was added. The coagulation reaction was allowed to proceed for 240 seconds, and the coagulation time was calculated using the principles of the ACL. The measured coagulation time, or rate (To) represents the coagulative activity of the plasma sample.

In a second rotor, another sample from the same subject was processed as above, except that the $H_2O$ is replaced with a PROTAC® solution ( fractionated *Agkistrodon contortrix contortrix* venom, 0. 125 U/mL conc.). The coagulation time, or rate (Ta) was then measured.

The ratio of (Ta/To) or the difference (Ta-To) represents an index of the total functionality of the PC-PS inhibitor system.

As an example, the values given below were obtained by the method described in the example above, and represent the To, Ta, and % E.U.C. of patients with a deficiency of PC, PS or with an increased aPC resistance. The % E.U.C. for normal plasma is between 57 and 153.

| Defect | To | Ta | % E.U.C. |
| --- | --- | --- | --- |
| PC deficiency | 45.6 | 84.0 | 43 |
|  | 39.4 | 66.0 | 39 |
| PS deficiency | 49.2 | 50.0 | 1 |
|  | 49.0 | 58.0 | 13 |
| aPC resistance | 32.8 | 37.2 | 4 |
|  | 30.2 | 34.2 | 12 |

It will be apparent to those skilled in the art that various modifications and variations can be made in the kits and methods of the present invention without departing from the spirit or scope of the invention. Thus, it is intended that the present invention cover the modifications and variations of this invention provided that they come within the scope of the appended claims and their equivalents.

What is claimed is:

1. A non-quantitative screening method for determining the presence of a defect in the protein C pathway, including a deficiency of protein C or protein S or APC resistance, said method comprising:

a. adding to a plasma sample obtained from said subject (i) a first reagent comprising bovine thromboplastin in an amount sufficient to induce or activate coagulation in the plasma, (ii) a second reagent which activates endogenous protein C in the plasma, and (iii) a third reagent comprising a combination of calcium salts, phospholipids and tissue thromboplastin;

b. adding to a second plasma sample from the same said subject (i) said first reagent which activates or induces coagulation, (ii) a buffer or other material which does not activate protein C, and (iii) a third reagent comprising a combination of calcium salts, phospholipids and tissue thromboplastin;

c. measuring the time, rate, or both, necessary for conversion of endogenous fibrinogen to fibrin in the sample of step (a);

d. measuring the time, rate, or both necessary for conversion of endogenous fibrinogen to fibrin in the plasma sample of step (b);

e. calculating the difference or ratio between the times, rates or both, obtained in steps (c) or (d), f. performing steps (a), (b), (c) and (d) on a sample of normal control plasma; and g. determining the difference or ratio in the times, rates, or both, obtained in steps (e) and (f) wherein said difference is indicative of the thrombotic risk in said subject.

2. The method of claim 1 wherein said second reagent comprises a purified fraction of venom obtained from a venom producing organism.

3. The method of claim 2 wherein the venom is snake venom obtained from *Agkistrodon contortrix contortrix*.

4. A kit for non-quantitative screening for a defect in the Protein C pathway including a deficiency in protein C or protein S or APC resistance, said kit comprising:

a. a first container comprising: (i) a first reagent comprising bovine thromboplastin in an amount sufficient to induce or activate coagulation in a plasma sample obtained from said subject, (ii) a second reagent which activates endogenous protein C in the plasma, and (iii) a third reagent comprising a combination of calcium salts, phospholipids and tissue thromboplastin;

b. a second container for adding to a second plasma sample from said same subject (i) said first reagent, (ii) a buffer or other material which does not activate Protein C, (iii) a third reagent comprising a combination of calcium salts, phospholipids and tissue thromboplastin.

5. The kit of claim 4 wherein said second reagent comprises a purified fraction of venom obtained from a venom producing organism.

6. The kit of claim 5 wherein the venom is snake venom obtained from *Agkistrodon contortrix contortrix*.

* * * * *